US008430651B2

(12) United States Patent  (10) Patent No.: US 8,430,651 B2
Elmouelhi et al.  (45) Date of Patent: Apr. 30, 2013

(54) MULTI-MATERIAL SINGLE-PIECE ACTUATOR MEMBER FOR MINIATURE RECIPROCATING PISTON PUMP IN MEDICAL APPLICATIONS

(75) Inventors: Ahmed Elmouelhi, Maple Grove, MN (US); Bernard Q. Li, Plymouth, MN (US); James M. Haase, Maplewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 580 days.

(21) Appl. No.: 12/684,207

(22) Filed: Jan. 8, 2010

(65) Prior Publication Data

US 2011/0172646 A1 Jul. 14, 2011

(51) Int. Cl.
*F04B 17/04* (2006.01)

(52) U.S. Cl.
USPC .......................................................... 417/417

(58) Field of Classification Search .................. 417/44.1, 417/50, 417, 505; 604/890.1
See application file for complete search history.

(56) References Cited

U.S. PATENT DOCUMENTS

| 5,788,465 | A | 8/1998 | Luongo et al. |
|---|---|---|---|
| 5,832,731 | A | 11/1998 | Kuehnle |
| 6,264,439 | B1 | 7/2001 | Falk et al. |
| 6,454,548 | B2 * | 9/2002 | Falk et al. ..................... 417/417 |
| 6,595,756 | B2 * | 7/2003 | Gray et al. .................... 417/44.1 |
| 6,623,630 | B1 | 9/2003 | Staffler |
| 6,736,049 | B2 | 5/2004 | Cautenet et al. |
| 6,770,067 | B2 * | 8/2004 | Lorenzen et al. .......... 604/891.1 |
| 6,932,584 | B2 * | 8/2005 | Gray et al. ..................... 417/417 |
| 6,945,760 | B2 * | 9/2005 | Gray et al. ..................... 417/417 |
| 7,080,975 | B2 | 7/2006 | Besse et al. |
| 7,214,039 | B2 | 5/2007 | Angove |
| 7,217,105 | B2 | 5/2007 | Angove |
| 7,325,478 | B2 | 2/2008 | Cautenet et al. |
| 8,137,314 | B2 * | 3/2012 | Mounce et al. ............... 604/151 |
| 2006/0008365 | A1 | 1/2006 | Angove |
| 2006/0070880 | A1 | 4/2006 | Goudberg et al. |
| 2006/0120899 | A1 | 6/2006 | Sengun et al. |
| 2008/0019854 | A1 | 1/2008 | Haertl |
| 2008/0312595 | A1 | 12/2008 | Elmouelhi et al. |
| 2009/0048562 | A1 * | 2/2009 | Falk et al. ..................... 604/152 |

* cited by examiner

*Primary Examiner* — Nicholas Lucchesi
*Assistant Examiner* — Diva K Chander

(57) ABSTRACT

An implantable medical device including a two piece actuator member which comprises a monocrystaline piston and a magnetizable pole. The monocrystalline piston is positioned within a piston channel having a surface having a titanium-oxide layer. The monocrystalline piston is selectively movable within the piston bore to permit intake and output of fluids.

12 Claims, 7 Drawing Sheets

MULTI-MATERIAL SINGLE-PIECE ACTUATOR MEMBER FOR MINIATURE RECIPROCATING PISTON PUMP IN MEDICAL APPLICATIONS

TECHNICAL FIELD

This disclosure relates generally to a drug pump. More particularly and without limitation, this disclosure relates to an actuator member assembly for a drug pump drive mechanism.

DESCRIPTION OF RELATED ART

Implantable medical devices may be used to deliver an infusion media (e.g. a medication such as insulin) to a patient. Such devices include a drug delivery device that may be designed to be implanted into a patient's body to deliver predetermined dosages of the infusion media to a particular location within the patient's body, e.g. in the venous system, the spinal column, or within the peritoneal cavity.

One device of the type described above is a pump having a drive mechanism that includes an actuator member. The actuator member may include a piston configured to reciprocate within a piston channel when a solenoid coil is selectively energized and de-energized. When the solenoid is energized, magnetic flux causes the actuator member to move rapidly in a forward stroke motion resulting in the delivery of a predetermined dosage of infusion media from an outlet chamber to the patient. When the solenoid is de-energized, the lack of magnetic flux, coupled with a force of a spring or other return mechanism, allows the actuator member to return to a retracted position. The pressure within the piston chamber falls gradually during the return stroke motion, causing infusion media to flow from a reservoir and refill the piston chamber thereby preparing the pump for its next pumping or delivery stroke.

During the life of a pump as described, the drive mechanism may be required to function over millions of cycles. During such cycling, the actuator member undergoes repeated forward and reverse strokes, typically under high acceleration, during the energizing and de-energizing of the solenoid coil. These repeated motions and the fit between the piston and the piston channel may result in wear issues relating to the piston and the piston channel, which may reduce the life of the actuator member and thus the implantable medical device. A continued need therefore exists for drive mechanism designs that improve wear resistance and performance.

BRIEF SUMMARY OF THE DISCLOSURE

It is generally desirable to minimize the overall size and dimension of implantable devices so as to prevent or minimize tissue damage. An actuator designed for such an implantable device is necessarily delicate because the size of the actuator must likewise be small. Conventional materials used for medical application actuator members have utilized an actuator member made of a soft material or having a soft exterior. For example, ferrous materials, such as ferritic stainless steel, may include high corrosion resistance with lubricious properties to facilitate ease of reciprocation. However, these conventional actuator members may exhibit wear issues. In contrast to the conventional materials, in the present invention an actuator member piston comprised of a monocrystalline material such as sapphire that exhibits minimal wear.

The present disclosure provides an actuator member for a drug delivery device including a monocrystalline piston coupled to a magnetizable pole. In an embodiment, the monocrystalline piston may comprise a sapphire material.

Another embodiment includes a drive mechanism for a drug delivery device including an actuator member for delivering fluid through a hardened piston channel from an inlet to an outlet during a pumping stroke. The actuator member includes a piston coupled to a pole, the piston sized and shaped for placement in the piston channel. In an example the piston is coupled to the pole through a press fit engagement. A magnetic coil is provided for selective movement of the piston within the piston channel by a magnetic force of attraction of the pole.

In an embodiment, the piston channel may comprise a heat treated titanium bore. In one embodiment, the thermal treatment of the piston channel may be an oxygen diffusion process that forms an oxidized layer on the surface of the piston channel.

Another embodiment includes an apparatus for delivering a fluid, the apparatus having a housing, an inlet in the housing for receiving the fluid, an outlet in the housing for discharging the fluid, a piston channel having an oxidized layer formed within the housing through which the fluid flows from the inlet to the outlet, and an actuator member positioned within the housing and moveable between a first position and a second position. The actuator member drives the fluid stored in a piston chamber toward the outlet when the actuator member transitions from a retracted position to an advanced position, corresponding to the forward stroke. Preparing for the next fluid delivery stroke by filling up the chamber with the fluid generally occurs when the actuator member moves from the advanced position to the retracted position corresponding to the reverse stroke. The actuator member includes a monocrystalline piston and a suitable pole whereby the monocrystalline piston is coupled to the pole and moveable within the piston channel. The actuator member piston and pole are moved by a magnetic attraction of the pole to a magnetic coil located within the housing.

BRIEF DESCRIPTION OF THE DRAWINGS

Embodiments of the present disclosure will hereinafter be described in conjunction with the following drawings wherein like reference numerals denote like elements throughout.

DETAILED DESCRIPTION OF THE DISCLOSURE

The following description is exemplary in nature and is not intended to limit the scope, applicability, or configuration of the present disclosure in any way. Rather, the description provides practical illustrations for implementing exemplary embodiments of the present disclosure. The scope of the disclosure is defined by the appended claims. The disclosure relates to a drive mechanism assembly for a piston pump that includes an actuator member comprising a piston and a pole. One drive mechanism assembly of this type has been disclosed by the present assignee in U.S. patent application Ser. No. 11/761,673, filed on Jun. 12, 2007, and entitled "ARTICULATED ACTUATOR MEMBER FOR IMPLANTABLE PUMP," which is herein incorporated by reference in its entirety.

Figure 1:
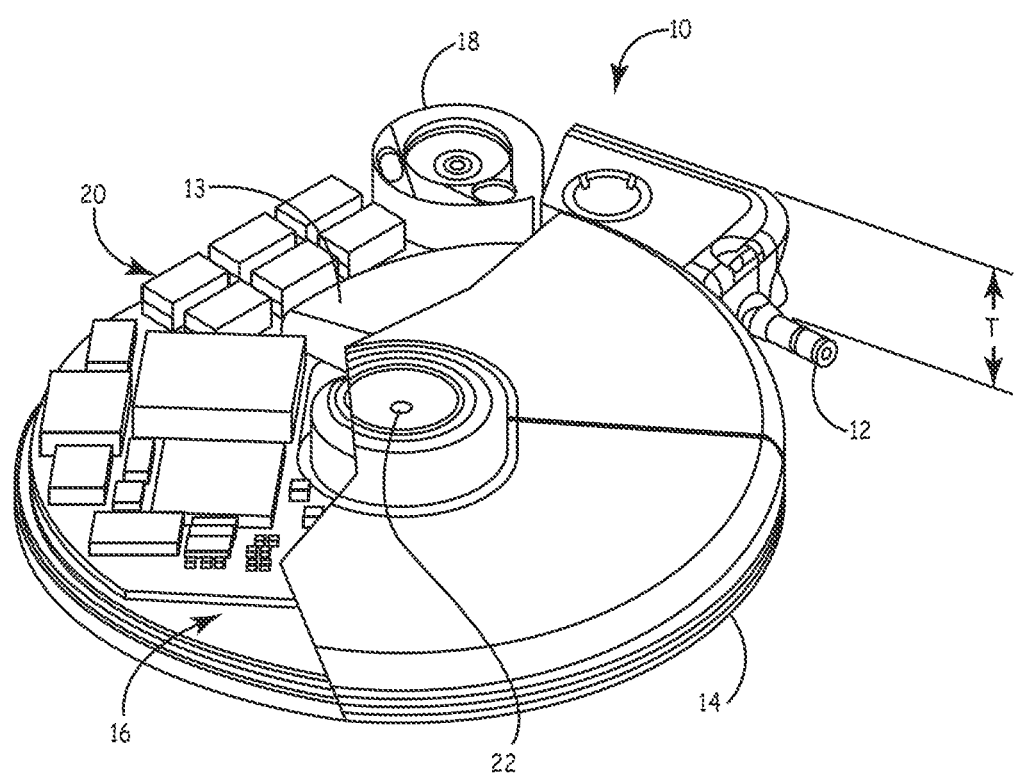
FIG. 1 is an isometric view of an implantable drug delivery device in accordance with one embodiment of the present disclosure.

FIG. 1 shows an implantable drug delivery device ("device") 10. Device 10 is configured to be surgically implanted into a patient, for example, in the abdominal region, between the skin and the abdominal wall. Connector 12 is coupled to a catheter 24 (FIG. 2) to deliver infusion medium to the patient, for example, but not limited to, by feeding infusion medium to a particular location in the venous system, within the spinal column, or in the peritoneal cavity of the patient. Other embodiments of the device 10 may be implemented as external drug delivery devices that connect to patients through suitable catheter devices or the like. Further embodiments of the device 10 may be used in other contexts, e.g., for delivery of a medium into other suitable environments. Therefore, for purposes of simplifying the present disclosure, the term "patient" is used herein to refer to any environment in which an implantable device is implanted or to which an external device is connected, whether or not the implant or connection is carried out for medical purposes. Also, the term "infusion medium" is used herein to refer to any suitable medium delivered by the device 10.

A description of the device 10 and how it is placed in the body may help to provide some further context for the present disclosure. The device 10 may include a generally disc-shaped enclosure 14. While a generally circular disc-shaped embodiment is illustrated in FIG. 1, it will be understood that further embodiments of enclosure 14 may employ other shapes, including, but not limited to, oval, oblong, rectangular, polygonal, or other geometric shapes. Generally, the enclosure 14 is made of a biocompatible material and most often has a relatively small diameter and thickness T to reduce patient trauma during implant surgery and after implantation. If implanted, the medical device 10 is typically positioned subcutaneously, e.g., from 1 centimeter (0.4 inches) to 2.5 centimeters (1 inch) beneath the skin, where there is sufficient tissue for supporting the medical device 10, e.g., with sutures or the like.

The enclosure 14 includes a reservoir 16 for holding a volume of infusion medium, such as, but not limited to, a liquid medication to be administered to the patient. Enclosure 14 may also contain a drive mechanism assembly 18 (e.g. a pump), a power source 13, and control electronics 20. Device 10 may be configured to receive infusion media from reservoir 16 via an inlet port 22. Inlet port 22 may provide a closeable and sealable fluid flow path to the reservoir 16. The inlet port 22 may include a sealable opening for receiving a needle through which fluid may be transferred to the drug delivery device, for example, to fill or re-fill the reservoir 16 with the infusion media or a rinsing fluid. In particular embodiments, the inlet structure 22 may be configured to re-seal after a fill or re-fill operation, and to allow multiple re-fill and re-seal operations. One example of inlet port 22 and reservoir 16 is described in U.S. Pat. No. 6,652,510, titled "Infusion Device and Reservoir for Same," which is incorporated by reference herein in its entirety. Typically, re-filling is accomplished with a non-coring needle connected to a syringe filled with a fluid. The needle may be inserted through the patient's skin and into a self-sealing septum located within the housing of the medical device 10.

In particular embodiments, both the drive mechanism 18 and the reservoir 16 may be hermetically sealed. In such embodiments, the enclosure 14 may be made from titanium or titanium alloy or other biocompatible metals. The reservoir 16 may be made from similar metals or a biocompatible and infusion medium compatible plastic that allows for the desired hermeticity.

Figure 2:
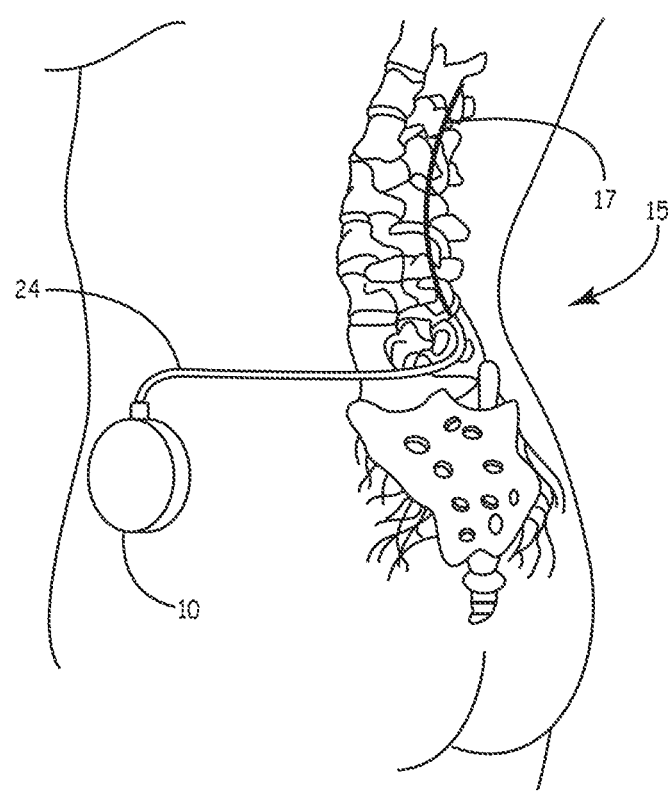
FIG. 2 is a representative view of a drug delivery device implanted into a body of a patient in accordance with one embodiment of the present disclosure

FIG. 2 illustrates an example placement of one embodiment of an implantable infusion system within a patient's body 15. The exemplary infusion system depicts device 10 in association with catheter 24. Such infusion systems may be used for a wide variety of therapies including treatment of pain, spasticity, and other medical conditions.

The medical device 10 and catheter 24 are typically implanted by a clinician (e.g., surgeon) within the body 15 during a surgical procedure. However, it should be noted that in other embodiments the present disclosure also contemplates embodiments wherein catheter 24 is implanted with a proximal end outside the body 15 coupled to the medical device 10 which is placed outside of the body 15, where the medical device 10 may be worn on a belt or removably attached to the outside of the patient's body 15.

Before implantation of the medical device 10, the catheter 24 may be positioned such that the fluid delivered to the patient through the catheter 24 reaches a selected internal delivery location 17 within the body 15 of the patient. As depicted, the infusion system is implanted such that the delivery site 17 is located within the intrathecal space of the spinal canal.

Figure 3:
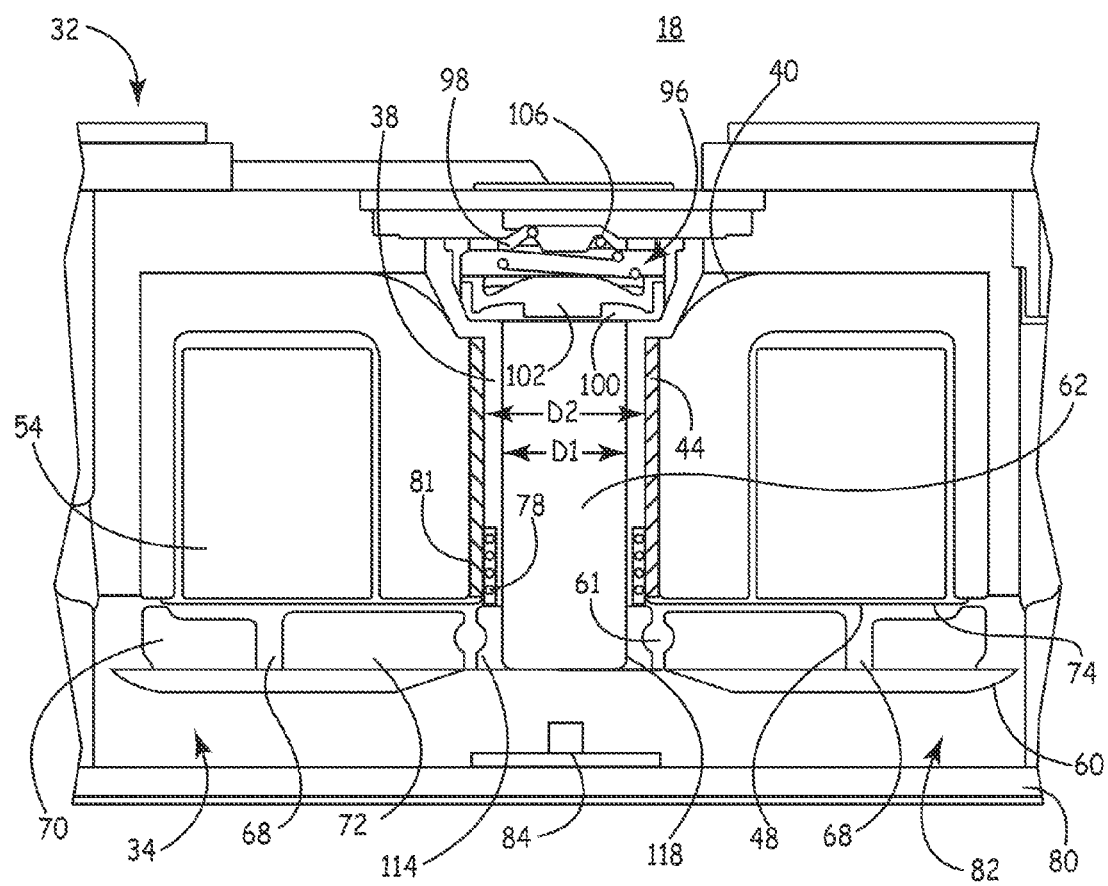
FIG. 3 is a cross-sectional view of a drive mechanism assembly in accordance with a first embodiment of the present disclosure.

FIG. 3 is a cross-sectional view of a drive mechanism 18 in a forward position or state. The forward state is the end of the pumping stroke that moves the infusion medium from the reservoir through an outlet and into the patient's body. The forward stroke, as previously discussed, is followed by a return stroke which completes a full pumping stroke. The pumping stroke rate is controlled to deliver infusion medium at a desired rate, for example, according to a programmed dispensing rate or schedule or according to an actuation signal from a sensor, timer or other suitable source.

Figure 4:
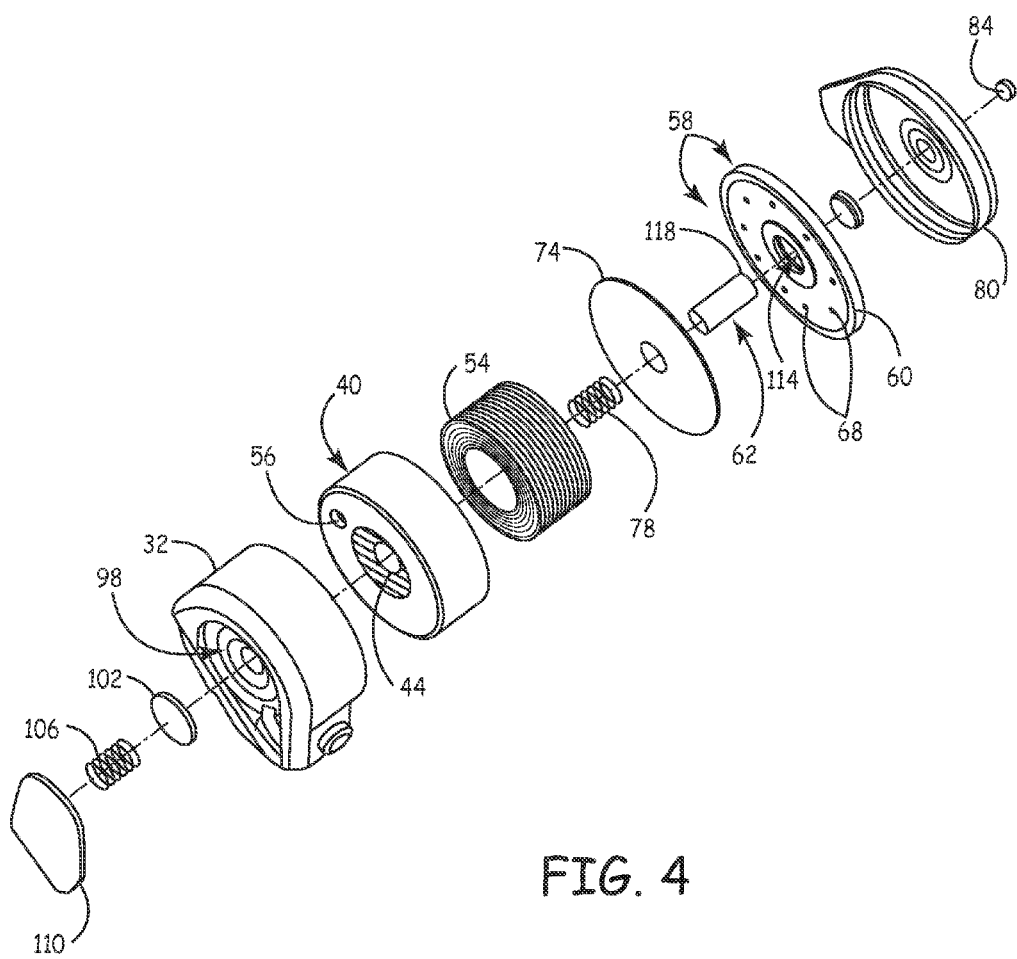
FIG. 4 is an exploded view of an embodiment of the drive mechanism assembly shown in FIG. 3.

Referring to FIGS. 3 and 4, the drive mechanism 18 includes a housing 32 that is open on one side to a hollow, annular interior section 34. The bottom side of the housing 32 (with reference to the orientation shown in FIG. 4) includes an open end to the interior section 34 (FIG. 3). In use, interior section 34 may be filled with the infusion medium to be delivered and refilled during and/or subsequent to each pump stroke. The housing 32 is most often made of generally rigid, biocompatible and infusion medium compatible material having no or low magnetic permeability such as, but not limited to, titanium, stainless steel, bio-compatible plastic, ceramic, glass or the like.

A coil cup 40 is located within housing 32. The coil cup 40 has a generally cylindrical shape, open on one end to a hollow, annular interior. When assembled, coil cup 40 is located in the hollow interior of the housing 32. A coil 54 is located within the hollow, annular interior of coil cup 40 and disposed around the axis of the coil cup 40. The coil cup 40 is provided with an opening 56 through which a lead extends to couple the coil 54 to an energy source such as power source 13 (FIG. 1). The coil 54 defines a surface that cooperates with an adjacent surface of a pole 60 to provide a path for electromagnetic flux during the forward stroke of the drive mechanism 18.

In some embodiments, coil cup 40 is made of generally rigid material having a relatively high magnetic permeability such as, but not limited to, low carbon steel, iron, nickel, ferritic stainless steel, ferrite, other ferrous materials, or the like. Coil 54 may include a conductive wire wound in a coil configuration. The coil wire may include any suitable conductive material such as, but not limited to, silver, copper, gold or the like, with each turn electrically insulated from adjacent turns and the housing 32. In one embodiment, the coil wire has a square or rectangular cross-section to achieve minimal space between windings and a greater number of coil turns thus improving electrical efficiency.

The housing 32 includes a sleeve 44 which has a piston channel 38 that extends axially relative to the length dimension of housing 32. In one embodiment, sleeve 44 is formed integrally with coil cup 40. However, in other embodiments, sleeve 44 is formed as a separate component that may be subsequently assembled into coil cup 40 through any suitable bonding, fusion or other similar process.

Figure 5A:
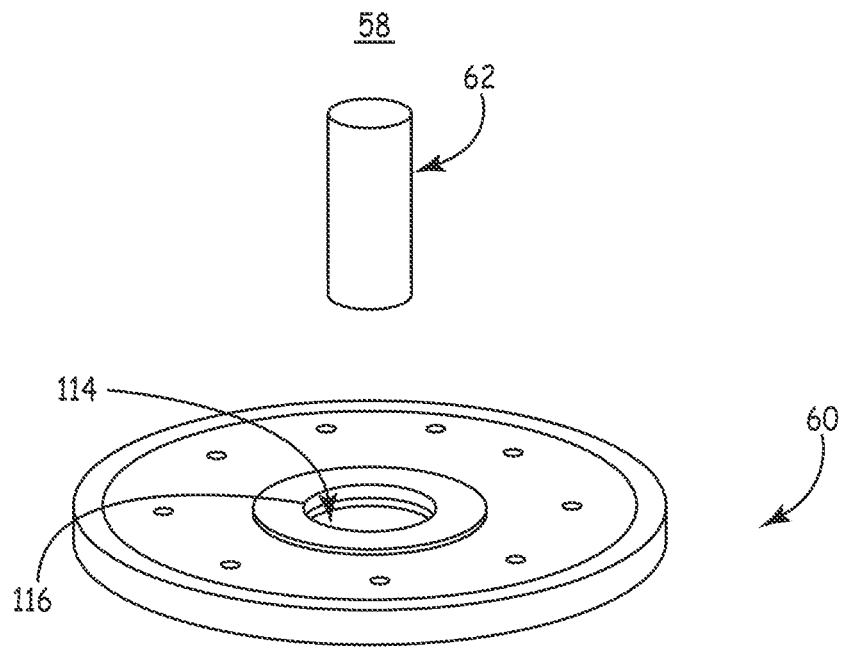
FIG. 5A is an exploded perspective view of one embodiment of an actuator member of the present disclosure.
Figure 5B:
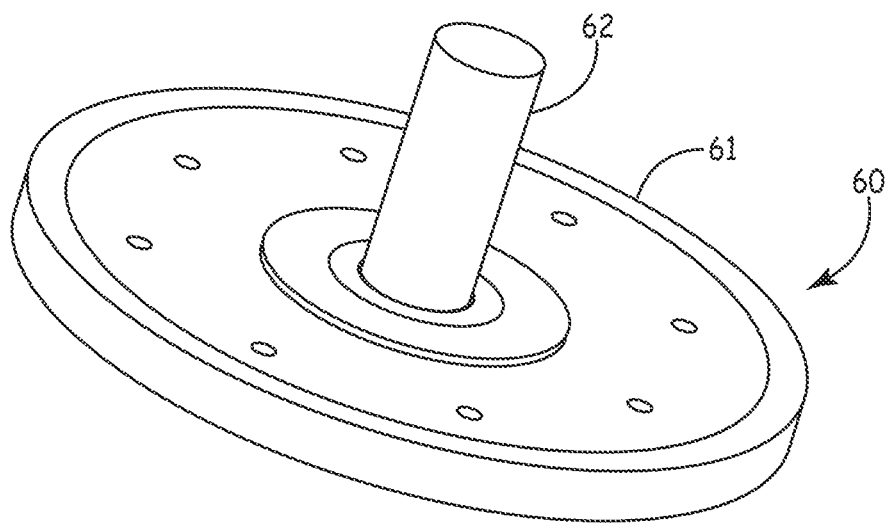
FIG. 5B is a perspective view of the embodiment shown in FIG. 5A.

As shown in FIGS. 5A and 5B, the drive mechanism 18 includes an actuator member 58, which includes a pole 60 and a piston 62. The pole 60 is a generally flat disk with a receiving portion 114 for receiving the piston 62. The receiving portion 114 is generally formed in the center of the pole 60 and is sized to conform to the cross-sectional size of piston 62. The receiving portion 114 in some embodiments may or may not be created through the entire width of pole 60. The pole 60 is made of a generally rigid, biocompatible and infusion medium compatible material having a relatively high magnetic permeability such as, but not limited to, ferrous materials, ferritic stainless steel with high corrosion resistance, or the like. The unique details of the present invention actuator member 58 are further described below.

Piston 62 is generally formed as a cylindrical rod with a diameter D1 that is sized to be slightly less than diameter D2 of sleeve 44. As further discussed below, the dimensions D1 and D2 are selected to provide a predetermined gap, defined by the difference between D1 and D2, such that during each return piston stroke the fluid will pass around the piston 62 to fill an outlet chamber 98 and will inhibit backflow during the forward piston stroke to help deliver a known volume of infusion medium. Piston 62 has a cross-sectional size in the range of about 0.5 millimeters to about 3.0 millimeters and a length in the range of about 4.0 millimeters to about 8.0 millimeters. The pump can provide an output flow ranging from about 0.5 microliters to about 1.0 microliter, per stroke, at a pressure of about 1.0 bar.

The pole 60 cooperates with the inner and outer walls of the coil cup 40 to provide a flux path for electromagnetic flux. The inner and outer walls of the coil cup 40 define a first pair of annular pole surfaces while the inner perimeter and outer perimeter edges of pole 60 define a second pair of pole surfaces. An actuator member spring 78 is provided to bias the actuator member 58 away from the coil cup 40 to provide a gap between the first and second pairs of pole surfaces. Holes 68 are provided in the pole 60 to provide radial paths for electromagnetic flux between an outer pole section 70 and an inner pole section 72. The flux path is everywhere on the pole 60 except for at the holes 68. The configuration of holes 68 is most often designed to provide a sufficient conductor for electromagnetic flux and yet minimize or reduce viscous resistance to actuator member 58 motion. With reference to FIG. 3, actuator member 58, including the assembled piston 62 and pole 60, is arranged with the piston 62 extending through the piston channel 38 and with the pole 60 positioned adjacent to the open side of the coil cup 40. When so positioned, a single stroke of the actuator member 58 during use of the pump will deliver a known volume of infusion medium based upon, for example, the free volume in the interior section 34.

The details of the present invention actuator member 58 in combination with the piston 62 and the pole 60 are further discussed below.

The actuator member spring 78 may be positioned around and coaxial to force pole 60 in the direction away from the open side of the coil cup 40 and provide a space between the pole 60 and the open side of the coil cup 40. A biocompatible and infusion medium compatible barrier 74 is located over the open side of the coil cup 40 between the pole 60 and the coil cup 40 to help seal the annular interior of the coil cup 40 and coil 54. In other embodiments in which infusion medium may contact the coil, the barrier 74 may be omitted.

The actuator member spring 78 in the illustrated embodiment is disposed partially within piston channel 38 to abut a shoulder 81. When assembled, actuator member spring 78 is disposed around piston 62 proximately adjacent to pole 60 such that one end of the coil spring abuts pole 60, while the opposite end distends from the channel 38. In this manner, actuator member spring 78 imparts a spring force between the housing 32 and the actuator member 58 to compete a return stroke. As may be appreciated, the actuator member spring 78 may be positioned at any other position that causes the piston 62 and the actuator member 58 to complete the return stroke.

Furthermore, in the illustrated embodiment, by partially disposing actuator member spring 78 within the piston channel 38, the actuator member spring 78 may have minimal or no contribution to the overall thickness dimension of the drive mechanism. The actuator member spring 78 is most often made of a biocompatible and infusion medium compatible material that exhibits a suitable spring force such as, but not limited to, titanium, stainless steel, MP35N-cobalt based alloy, or the like.

The drive mechanism 18 may further include a cover 80 which attaches to the housing 32 over the open side of the housing 32 and the barrier 74. The cover 80 is most often made of a generally rigid, biocompatible and infusion medium compatible material having a relatively low magnetic permeability (being relatively magnetically transparent) such as, but not limited to, titanium, stainless steel, biocompatible plastic, ceramic, glass or the like.

The cover 80 seals the interior section 34 between the barrier 74 and the bottom side of the housing 32. Pole 60 resides within the interior section 34 when cover 80 is attached to the housing 32. The pole 60 is moveable in the axial direction within the interior section 34 between the forward position of the forward stroke and the retracted position of the reverse stroke. This movement is created by the action of electromagnetic force generated when a current is passed through the coil 54 and the mechanical return action of the actuator member spring 78.

An adjusting stop 84 is located within cover 80 for contacting pole 60 when the pole 60 is in the fully retracted position to set the retracted position of pole 60. In particular embodiments, a seal (not shown) (e.g. a silicon rubber sealing ring) may be disposed between the stop 84 and the cover 80. In further embodiments, a flexible diaphragm (not shown)

(such as, but not limited to, a thin titanium sheet or foil) may be coupled to the inside surface of the cover 80 and sealed around the opening through which the stop 84 extends. The diaphragm will flex to allow stop 84 to define an adjustable retracted position while also providing sealing functions for inhibiting leakage at the interface between stop 84 and cover 80. In other embodiments, after a proper pole 60 position is set, stop 84 is fixed in place with respect to the cover 80, for example, by adhesion of stop 84 to cover 80 with one or more welds, adhesives or other securing methods.

As shown in FIG. 3, piston 62 extends in the piston channel 38 toward an outlet at the end of the piston channel 38. Sleeve 44 has an inside diameter D2 that is larger than the outside diameter D1 of piston 62. As a result, a gap is defined between the piston 62 and the wall of the sleeve 44 along the length of the piston channel 38. The interior section 34 is in fluid communication with the piston chamber 100 and the space defined between piston 62 and the wall of sleeve 44. Fluid is present in the interior section 34, travels through the gap between D1 and D2, and into an outlet chamber 98. Magnetic flux on coil 54 creates a magnetic force that attracts pole 60 causing actuator member 58 to move in the direction toward valve assembly 96, or forward stroke. The forward stroke causes fluid to be delivered from the interior section 34 through the gap between piston 62 and the wall of the sleeve 44 and out of the drive mechanism 18 through piston chamber 100.

In the return stroke, the coil 54 is demagnetized and the spring 78 forces actuator member 58 towards cover 80. Thus the selective energizing and de-energizing of the coil 54 causes actuator member 58 to reciprocate within piston channel 38 in a repeatable linear path, stroke after stroke. In the return stroke, infusion medium in the volume of cup 80 flows into the annular volume, around the actuator member 58 and through holes 68 of the actuator member 58 in preparation for the next delivery.

In particular embodiments, the gap defined by the spacing between D1 and D2 is selected to provide a suitable flow toward the piston chamber 100 to refill the piston chamber 100 (during a return stroke of the piston), but small enough to sufficiently inhibit back flow of medium from the piston chamber 100 (during the forward stroke of the piston). The actual spacing between the piston 62 and the wall of sleeve 44 that permit such a result depends, in part, on the overall dimensions of those components, the pressure differentials created in the mechanism, and the viscosity of the infusion medium.

The valve assembly 96 in the embodiment of FIG. 3 may further include the valve member 102 and a valve spring 106. The valve member 102 is located within the outlet chamber 98 and, as shown in FIG. 3, is positioned close to the opening between piston channel 38 and outlet chamber 98 when actuator member 58 is in the forward position. During the forward stroke, valve member 102 is positioned to open a flow passage between piston channel 38 and outlet chamber 98. Valve spring 106 is located within outlet chamber 98 to support valve member 102. Spring 106 imparts a spring force on valve member 102 in the direction toward piston 62, urging valve member 102 toward a closed position to block the opening between piston channel 38 and outlet chamber 98.

Valve member 102 is most often made of generally rigid, biocompatible and infusion medium compatible material, such as, but not limited to, titanium, stainless steel, biocompatible plastic, ceramic, glass, gold, platinum or the like. A layer of silicon rubber or other suitable material may be attached to the rigid valve member 102 on the surface facing the channel 38 to help seal the opening to piston channel 38 when valve member 102 is in the closed position shown in FIG. 3.

Valve spring 106 is most often made of biocompatible and infusion medium compatible material that exhibits a suitable spring force such as, but not limited to, titanium, stainless steel, MP35N cobalt steel or the like. In the illustrated embodiment, valve spring 106 is a coil spring. In other embodiments, other suitable valve spring configurations may be employed, including, but not limited to, helical, flat, radial, spiral, barrel, hourglass, constant or variable pitch springs or the like.

In the present embodiment, drive mechanism 18 employs the electromagnetic force generated by coil 54 to move between the reverse position and the forward position to cause infusion medium to be drawn into and driven out of pump 18 and infusion device 10 in a controlled manner.

During the operational life of a device 10, the pumping system may be required to complete pump strokes millions of times. To reduce wear on the piston 62 and the piston channel 38 of the sleeve 44, the piston 62 in the present embodiment is made of a monocrystalline material that is also biocompatible and infusion medium compatible. In one embodiment, such a material is a single-crystal material such as sapphire. Sapphire exhibits an extremely hardened surface with a high degree of compatibility with known infusion mediums. Furthermore, sapphire may be preferable for pumping pistons in medical device applications because a sapphire piston 62 does not wear away the surface of the piston channel 38. The sapphire piston 62 may also be manufactured with extremely tight tolerances for length, width, and circularity, in contrast to pistons 62 that are formed integrally with pole 60. Such a piston 62 may be readily fit to a separately manufactured pole 60 to produce an actuator member 58 with a high degree of design tolerance.

In further embodiments, other materials may also be used to make piston 62 such that, in combination with pole 60, a very hard and wear resistant actuator member 58 with a high degree of accuracy is achieved. Other materials may include other single crystal materials such as ruby, or polycrastalline ceramics such as aluminum oxide, zirconium oxide, silicon oxide, magnesium oxide or ytterbium oxide. Alloys such as MP35N, surgical grade cast F-75 cobalt-chromium-molybdenum, or zirconium may alternatively be used. Additional materials may comprise titanium composites of a titanium base alloys reinforced with particles such as carbon, graphite, or oxygen, hard ceramics such as zirconia or alumina or carbides.

In the present embodiment the pole 60 is manufactured entirely, partially, or substantially of a biocompatible material with a relatively high magnetic permeability, such as ferritic stainless steel. Because the pole 60 is manufactured separately from the piston 62, the pole may be machined to very strict dimensional tolerances. Moreover, a pole receiving portion 114 may be made substantially in the center of the pole 60 to receive the piston 62.

The piston 62 is secured to the pole 60 receiving portion 114 at a proximal portion 118 through press fit coupling or frictional engagement. In further embodiments no permanent coupling is necessarily established between the piston and the pole. The term "assembled" should therefore not be limited to making a permanent or locking type engagement of the pieces of the actuator member but instead may only imply arrangement of the pieces in a manner designed to perform the pumping function.

A particular advantage of the tight tolerances in which the separately manufactured piston 62 and pole 60 are created allows for the piston 62 top be secured to the pole 60 through press fit or other frictional engagement without the use of any additional adhesive or mechanical fastening device, such as a rivet. Since piston 62 is typically cylindrical, receiving portion 114 is circular with a slightly smaller diameter than that of piston 62 to permit the press fit engagement of piston 62. In other embodiments other conventional coupling techniques may be also used. As may be appreciated, the piston 62, and pole 60 may be formed of any size and shape. For example, piston 62 may have a spherical or cubical cross-sectional shape with a correspondingly shaped receiving portion 114.

To further reduce wear of actuator member 58 while realizing the full benefits of titanium alloys in the friction and wear applications contemplated by the present disclosure, surface modification treatments may be made to one or both of the reciprocating surfaces of piston 62 and/or the interior surface of sleeve 44 that defines the piston channel 38. The surface modification treatments effectively increase the near-surface strength and thereby lower the tendency for material transfer and adhesive wear. As such, the reduced wear resulting from the surface modification treatment also reduces the coefficient of friction and thereby increases the pumping efficiency of actuator member 58. Numerous processes and materials for surface modification treatment exist including thermal treatment, ion implantation, lubrication, polishing, material deposition, coating or the like.

In one embodiment, the sleeve 44 may undergo a thermal oxidation process that forms an oxide layer such as titanium oxide on the surface of piston channel 38 of the sleeve 44 to decrease wear. An example of such an oxidation process is described in U.S. Pat. No. 6,210,807, entitled "Surface oxidation of titanium or titanium alloy article," which is incorporated herein by reference in its entirety. The thermal oxidation process forms a hard layer on the interior surface of sleeve 44. The oxide layer cooperates with the material of the piston 62 when the piston 62 is reciprocated within channel 38 to minimize or eliminate wear. In one embodiment, a hard layer, such as titanium oxide is achieved at a temperature in the range of about 600° C. to about 650° C. for a set period of time. More particularly, in one embodiment a titanium oxide layer is formed by treating the titanium at 550° C. for 60-65 hours in a controlled gas mixture comprising approximately 50% to 80% argon and 20% to 50% oxygen. In another method the titanium is treated at 500° C. for 60-65 hours with a similar gas mixture to form the titanium oxide layer. In alternative embodiments the thermal oxidation process may be carried out utilizing normal atmospheric air. In yet other embodiments, the argon in the argon gas mixtures above may be substituted for nitrogen gas.

In some embodiments, the thermal oxidation of piston channel 38 is typically performed with the sleeve 44 having being assembled into coil cup 40 through any suitable bonding, fusion or other similar process. The oxide layer substantially reduces or eliminates wear of sleeve 44 and piston 62 that results from the stroke motions.

An alternative embodiment for formation of a hard layer on the interior surface of sleeve 44 defining piston channel 38 may include a titanium nitriding process. However, in one or more implementations contemplated for the construction of drive mechanism 18, the oxidation process is preferable to the nitriding surface treatment. The construction of drive mechanism 18 typically includes bonding sleeve 44 to coil cup 40 through press fit coupling. The press fit coupling requires tight tolerance specifications to achieve the appropriate bonding between sleeve 44 and coil cup 40. The tolerance specifications for sleeve 44 and coil cup 40 are easily controlled if the bonding is performed prior to performing the nitriding surface treatment. However, if the nitriding treatment of sleeve 44 is performed prior to the press fit bonding, the nitriding treatment will result in formation of a nitride layer on both the interior and exterior surfaces of sleeve 44. The formation of a nitride layer on both the interior and exterior surfaces may make it hard to predict and control the coupling dimensions to achieve the appropriate interference fit and therefore presents a manufacturing challenge. As such, it is preferable to perform the surface treatment of piston channel 38 on sleeve 44 subsequent to the press fit coupling.

In addition, the nitriding process involves a heat treatment process with high temperatures in excess of 800° C. The high temperature required for the nitriding process makes the process unsuitable for an assembled sleeve 44 with the coil cup 40 because the coil 54 that is disposed in the coil cup 40 is susceptible to alteration of its magnetic properties by the high temperatures. As discussed above, the oxidation surface treatment process can be performed in relatively lower temperatures, thereby avoiding the deleterious effects on coil 54. As such, the oxidation process is preferable to the nitriding process for the surface modification treatment of the piston channel 38.

In an alternative embodiment, a lubricious layer (not shown) may alternatively or additionally be disposed on the surface of piston channel 38 to reduce the coefficient of friction between piston 62 and the channel 38 surface. In an example, the lubricious layer comprises an amorphous carbon film (diamond-like-carbon films/DLC). Any other known coating processes including physical vapor deposition, chemical vapor deposition, and plasma enhanced chemical vapor deposition may be used to coat a layer of material such as TiN, TiCN, TiAlN, CrN, AlTiN, CrCN, ZrN, Al2O3, or other similar wear resistant coatings.

Figure 6:
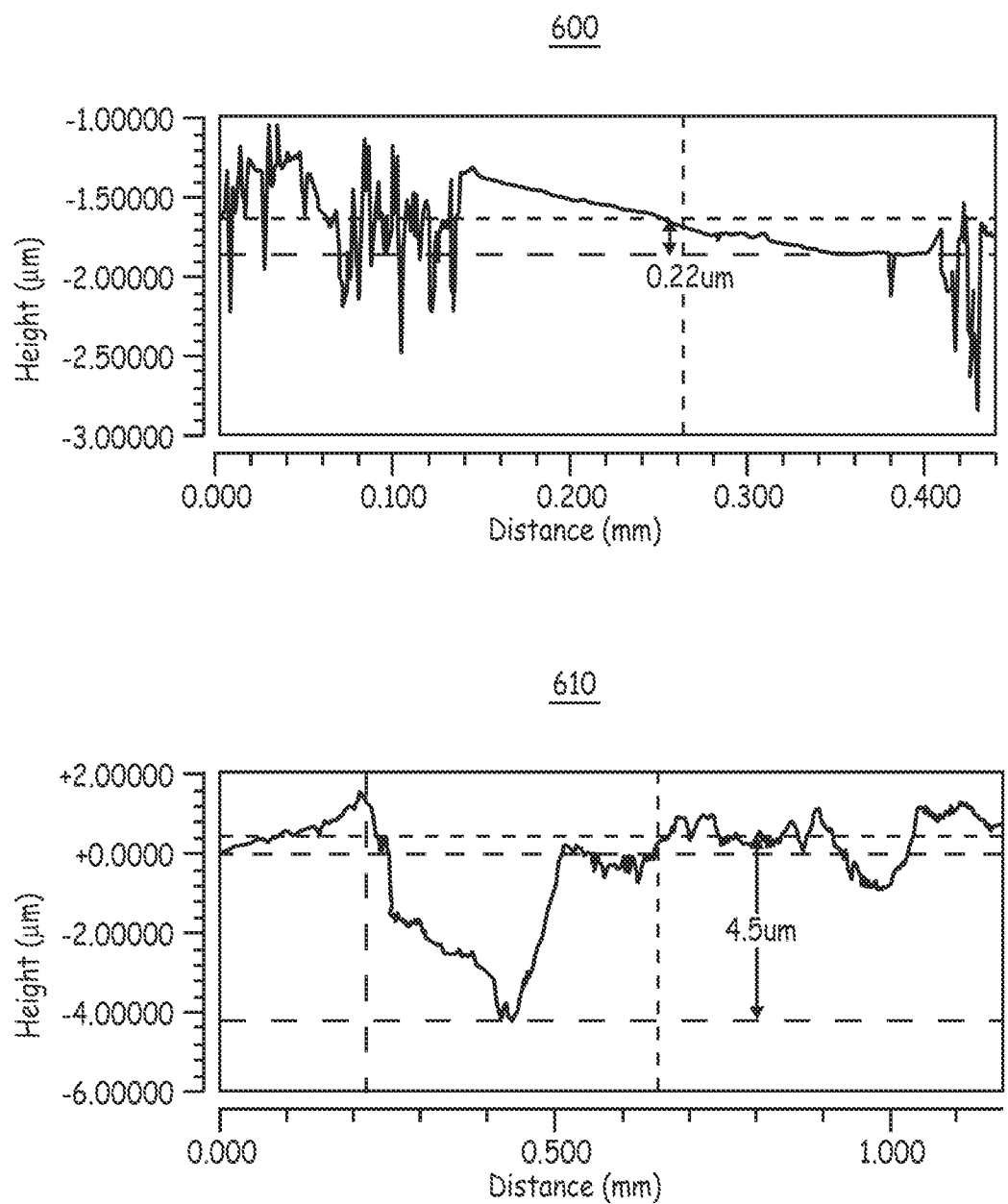
FIG. 6 illustrates the results of comparative wear experiments performed on the surfaces of a treated sleeve and an untreated sleeve of a drive mechanism assembly.

FIG. 6 illustrates results of an analysis of comparative wear experiments performed on surfaces of a treated sleeve 44 and an untreated sleeve 44. Specifically, chart 600 corresponds to the results of a thermally oxidized titanium sleeve 44 whereas chart 610 corresponds to the results of an untreated titanium sleeve 44.

The results from chart 600 were obtained from a wear experiment of a drive mechanism 18 that was constructed with piston 62 formed from sapphire and sleeve 44 having a piston channel 38 surface that had undergone thermal oxidation as described in relation to FIG. 5, above, at a temperature of 550° C. for 63 hours. The piston 62 was positioned within the piston channel 38 with an off-center loading at 0.01 inches. The drive mechanism 18 was operated for 500,000 cycles to deliver a saline fluid. Subsequent to the operation, the treated sleeve 44 was cut in half and the surface of piston channel 38 was examined to determine the wear characteristics.

As illustrated in chart 600, the wear depth of the sleeve 44 that had undergone a thermal oxidation surface treatment was approximately 0.22 μm. The wear was found to extend over a length of 0.27 μm on the surface of the treated piston channel 38.

For comparison, a second drive mechanism 18 was constructed having a piston 62 formed from a stainless steel alloy (AL 29-4). The piston channel 38 of titanium sleeve 44 was left untreated. The drive mechanism 18 was operated for 500,000 cycles delivering a saline fluid. Initially, the piston 62 was positioned within the piston channel 38 with an off-center loading of 0.01 inches. However, after 133,000 cycles, the piston 62 jammed within the piston channel 38 due to excessive wear of the surface of channel 38. Thereafter, the piston 62 was repositioned and centrally aligned within the piston channel 38 and operated for the remaining 377,000 cycles. Upon completion of the 500,000 cycles, the untreated sleeve 44 was cut in half for examination of the untreated surface of piston channel 38.

The comparative results of chart 610 illustrate that the wear depth on the surface of piston channel 38 was about 4.5 µm with the wear extending over a length of 1.2 µm on the channel 38. Overall, the wear volume of the thermal oxidation treated bore was about 0.000039 mm$^3$ which was found to be about 100 times less than the worn volume of 0.0039 mm$^3$ of the untreated bore.

The results of the comparative wear testing of the treated and the untreated surfaces of the piston channels confirmed that the treated surface has a much higher (by a factor of about 100) wear resistance times making it better suited for the present disclosure.

Figure 7A:
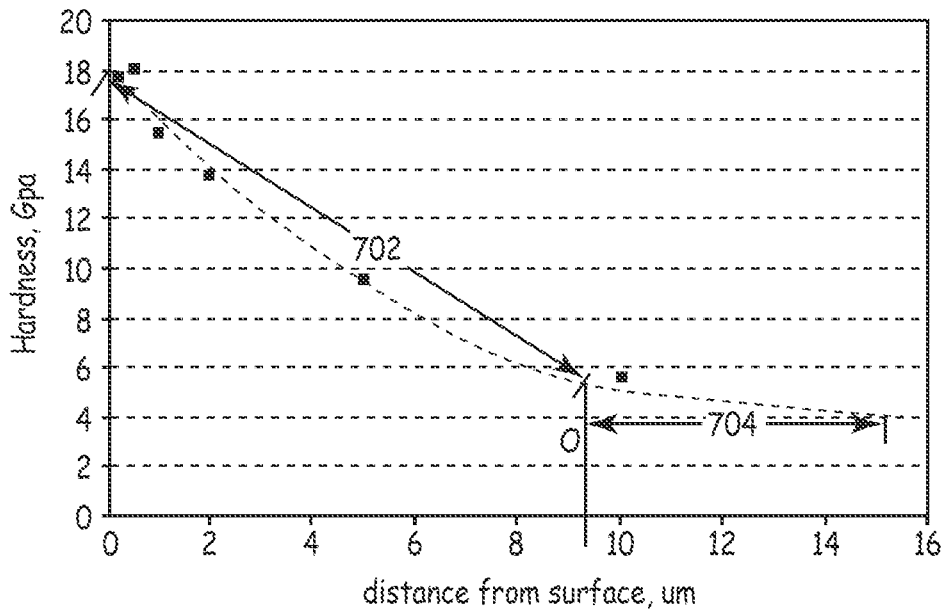
FIGS. 7A and 7B illustrate exemplary hardness profiles of the surfaces of a first sleeve treated with an oxidation surface treatment and a second sleeve treated with a nitriding surface treatment.
Figure 7B:
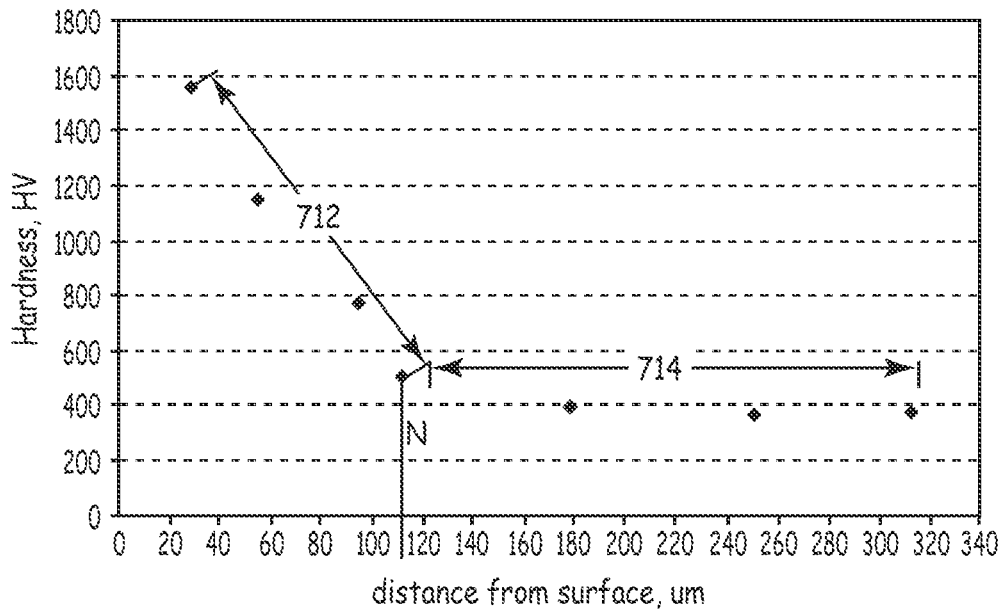

FIGS. 7A and 7B illustrate exemplary hardness profiles of the surfaces of two sleeves 44 in yet another experiment. The experiment was performed on two sleeves 44 having a base titanium material. The first sleeve 44 had a piston channel 38 treated with a thermal oxidation process as described in relation to FIG. 5, above, and the second sleeve 44 had a piston channel 38 treated with a titanium nitriding surface treatment. In the experiment, different processes were utilized to measure the resulting thicknesses and hardness of the oxide and nitride layers. As such, the units on the Y-axis represent the hardness of the two layers.

FIG. 7A depicts a profile 700 illustrating the results of the hardness profile of sleeve 44 treated with the oxidation surface treatment. The hardness of the oxide layer represented on the Y-axis was measured in gigapascal (GPa) units. The build up of the oxide layer on the surface of sleeve 44 is represented by a section 702 on the profile 700. In the experiment the resulting oxide layer represented by section 702 was approximately 5-10 µm thick. A section 704 of the profile 700 represents the titanium-base sleeve 44 diffused with oxide particles. As demonstrated in the profile 700, the oxide particles were found to have been diffused into the titanium-base sleeve 44 to a depth of about 6.0 µm.

FIG. 7B depicts a profile 710 illustrating the results of the hardness profile of sleeve 44 treated with a nitriding surface treatment. Because the nitriding process resulted in a thicker layer (X-axis) relative to the thickness of the oxide layer, a Vickers Hardness (HV) testing method was used to determine the hardness of the resulting nitride layer. Thus, the hardness of the nitride layer represented on the Y-axis was measured in HV units. For comparison purposes, the GPa units are converted to HV units by multiplying the GPa value with a constant of 102. Section 712 on the profile 710 represents the build up of the nitride layer that was formed on the surface of sleeve 44. In the experiment, the nitride layer build up exceeded 100 µm in thickness, as measured from the surface of sleeve 44. A section 714 on the profile 710 represents the titanium-base sleeve 44 diffused with nitride particles.

The results of the comparative experiment demonstrate that the resulting oxide layer section 702 was much thinner than the nitride layer. The thick titanium nitride layer, relative to the titanium oxide layer, affects the construction drive mechanism 18. Owing to the relatively thicker build up of the titanium nitride layer (represented by section 712) as compared to the titanium oxide layer (represented by section 702), the sizing of the diameter of either piston 62 or sleeve 44 must be adjusted for proper operation of the drive mechanism 18. Specifically, the thicker nitride surface in contrast to the oxide surface dictates either a reduction in diameter of the piston 62 or an increase in the diameter of the sleeve 44 to compensate for the thicker layer.

The deposition of the nitride layer was also observed to result in an uneven sleeve 44 bore surface having cracks and hard nodules. The uneven nitride surface layer was determined to be unsuitable for the drive mechanism because the cracks and the hard nodules cause abrasion of the piston 62 causing the piston 62 to wear. As depicted in the experimental results, the oxidation treatment on the other hand deposits a relatively smaller layer that was found to uniformly cover the surface of the base titanium piston 62. As such the thermal oxidation treatment of sleeve 44 produced a smoother surface that would prolong the life of the drive mechanism 18.

Further, as the oxide layer wore down, the titanium oxide base was found to be smoother resulting in decreased energy consumption per stroke volume. It is to be expected that the gradual wear down of the nitriding surface will expose the hard nodules and cracks on the surface causing excessive wear on the piston 62.

In the present disclosure, the piston 62 and the pole 60 that form the actuator member 58 may be manufactured separately and then assembled together to form the actuator member 58. In one embodiment, the actuator member 58 may be separately formed as two or more pieces and then assembled before or after placement into the device 10. Manufacturing the piston 62 and the pole 60 as separate components may provide for improved form, such as length, width, and circularity tolerances, of the overall actuator member 58 when manufactured as one unit. In addition, manufacturing the piston 62 and pole 60 as separate parts may improve their perpendicularity when assembled, resulting in reduced wear during pumping. As may be appreciated, the pole 60 and piston 62 may also be referred to by other names without affecting the scope of the present disclosure, such as, for example, the pole may be known as an armature.

While at least one exemplary embodiment has been presented in the foregoing detailed description of the disclosure in the context of a drug pump, this is merely for the sake of simplicity and ease of illustration. It should be appreciated that a vast number of variations exist. For example, in further embodiments the actuator member may be included in any type of pumping system, including those not related to drug delivery devices.

It should also be appreciated that the exemplary embodiment or exemplary embodiments are only examples and are not intended to limit the scope, applicability, or configuration of the disclosure in any way. Rather, the foregoing detailed description will provide those skilled in the art with a convenient road map for implementing exemplary embodiments of the disclosure, it being understood that various changes may be made in the function and arrangement of elements described in an exemplary embodiment without departing from the scope of the disclosure as set forth in the appended claims and their equivalents.

What is claimed is:

1. An implantable medical device, comprising:
   a housing;
   a reservoir disposed within the housing;
   a drive mechanism assembly coupled to the housing, comprising:
     a sleeve having a hollow piston channel, the surface of the channel including an oxidized layer and a lubricious layer disposed over the oxidized layer;
     a two piece actuator member, the actuator member comprising:
       a bio-compatible monocrystalline piston axially disposed within the piston channel bore; and
       a magnetizable pole coupled to an end of the piston.

2. The device of claim 1, wherein the bio-compatible monocrystalline is sapphire.

3. The device of claim 1, wherein the bio-compatible monocrystalline is ruby.

4. The device of claim 1, further comprising a lubricious layer disposed over the oxidized layer.

5. The device of claim 1, wherein the piston is coupled to the pole through press fit coupling.

6. The device of claim 1, wherein the piston is moveable within the piston channel upon magnetic attraction of the pole.

7. A pump assembly for delivery of an infusion medium, comprising:
- a pump housing open on one side to a hollow interior section;
- an actuator member sleeve disposed within the housing having a piston-receiving channel, wherein a surface of the channel comprises an oxidized layer and a lubricious layer disposed over the oxidized layer;
- a two piece actuator member assembly including:
  - a bio-compatible monocrystalline piston axially disposed to reciprocate within the piston-receiving channel; and
  - a magnetizable pole coupled to the piston.

8. The pump assembly of claim 7, wherein the pole is secured to the piston through press fit coupling in a perpendicular orientation.

9. The pump assembly of claim 7, wherein the bio-compatible monocrystalline is sapphire.

10. The pump assembly of claim 7, wherein the bio-compatible monocrystalline is ruby.

11. The pump assembly of claim 7, wherein the bio-compatible monocrystalline piston is moveable within the piston-receiving channel upon magnetic attraction of the magnetizable pole to the sleeve.

12. The pump assembly of claim 7, further comprising a cover coupled to the housing substantially adjacent the open side of the housing.

* * * * *